United States Patent [19]
Wyatt

[11] Patent Number: 4,952,055
[45] Date of Patent: Aug. 28, 1990

[54] DIFFERENTIAL REFRACTOMETER

[75] Inventor: Philip J. Wyatt, Santa Barbara, Calif.

[73] Assignee: Wyatt Technology Corporation, Santa Barbara, Calif.

[21] Appl. No.: 252,331

[22] Filed: Oct. 3, 1988

[51] Int. Cl.[5] ..................... G01N 21/41; G01N 21/49
[52] U.S. Cl. ..................................... 356/73; 356/128; 356/130; 356/343
[58] Field of Search .................. 356/73, 128, 130, 133, 356/134, 338, 343

[56] References Cited

U.S. PATENT DOCUMENTS

| | | | |
|---|---|---|---|
| 3,619,068 | 11/1971 | Broerman | 356/130 |
| 3,636,360 | 1/1972 | Oishi et al. | 356/134 |
| 4,229,105 | 10/1980 | Silverbage | 356/130 |
| 4,448,691 | 5/1984 | Davis | 210/656 |
| 4,660,974 | 4/1987 | Mächler et al. | 356/128 |
| 4,710,643 | 12/1987 | Schukler et al. | 356/134 |
| 4,756,884 | 7/1988 | Hillman et al. | 422/73 |

Primary Examiner—F. L. Evans
Attorney, Agent, or Firm—Philip J. Wyatt

[57] ABSTRACT

A differential refractometer is described capable of measuring the refractive index charge, dn, of a transparent fluid corresponding to a change dc of the concentration of a solute in said fluid. The fluid is restricted to a fine capillary within a transparent material such as glass. Incident upon the capillary at an angle close to the critical angle is a fine light beam incident from said transparent material. The axes of the light beam and capillary intersect at a point within the capillary defining thereby a plane within which the refraction occurs. A position sensing device is placed to measure the displacement of the beam twice refracted during its passage through the capillary, said measure being used to generate a numerical value of the ratio dn/dc.

35 Claims, 7 Drawing Sheets

DIFFERENTIAL REFRACTOMETER

The present invention is directed to a method and apparatus of considerable utility for the determination of the refractive index of fluids that may contain dissolved substances and particularly when such substances result in a change of the refractive index of the fluid.

PRIOR RELATED PATENTS AND APPLICATION

Expressly incorporated by reference herein are the following related patents and application:

| | |
|---|---|
| U.S. Pat. No. | 4,490,042 |
| Title: | Method for Determining the Properties of Wine |
| Inventor: | Philip J. Wyatt |
| Filing Date: | June 4, 1981 |
| Issue Date: | December 25, 1984 |
| U.S. Pat. No. | 4,616,927 |
| Title: | Sample Cell for Light Scattering Measurements. |
| Inventors: | Steven D. Phillips, Jeffrey M. Reece and Philip J. Wyatt. |
| Filing Date: | November 15, 1984 |
| Issue Date: | October 14, 1986 |
| U.S. Pat. No. | 4,710,025 |
| Title: | Process for Characterizing Suspensions of Small Particles |
| Inventors: | Philip J. Wyatt and Gregory M. Quist |
| Filing Date: | September 9, 1985 |
| Issue Date: | December 1, 1987 |
| U.S. Pat. Application Ser. No. | 059,157 |
| Title: | Sample Cell Monitoring System |
| Inventors: | Philip J. Wyatt and Steven Phillips |
| Filing Date: | June 5, 1987 Continuation of Application 861,863, filed May 12, 1986, now abandoned: this is a division of Application Ser. No. 671,181, filed November 15, 1984, now Pat. No. 4,616,927. |

DEFINITIONS

The term "light" shall mean electromagnetic radiation.

The term "beam" or "ray" shall mean a pencil of light propagating in a parallel or nearly parallel direction.

The term "beam diameter" of an incident light source with a Gaussian intensity profile, such as a laser, shall refer to the diameter of the beam measured between the points at which the intensity has fallen to $1/e^2$ the intensity at the center of the beam.

The term "forward scattering direction" refers to the range of scattering angles less than 90 degrees with respect to the direction of the incident beam.

The term "backward scattering direction" refers to the range of scattering angles propagating at an angle greater than 90 degrees with respect to the direction of the incident beam.

For plane polarized light, the plane perpendicular to the direction of the electric field is called the "V-plane" and said plane polarized light is vertically polarized with respect to said perpendicular plane. The corresponding H-plane is perpendicular to the V-plane and contains the plane wave's incident electric field.

BACKGROUND OF THE INVENTION

Measurement of the refractive index of fluids, and especially the changes of said refractive indices when various substances are dissolved in said fluids at different concentrations, is an important requirement for a variety of physical determinations. For example, the determinations of molecular weights of dissolved molecules by light scattering techniques requires the measurement of $dn/dc$ for the dissolved molecules. This differential quantity represents the change of refractive index $dn$ of the solvent with a change of concentration $dc$ of the solute comprised of the molecules to be measured. In the area of liquid chromatography, the concentration of dissolved molecules that have been separated by appropriate columns is determined often by means of a refractive index detector. Such an instrument responds to the changes in fluid refractive index caused by changes in concentration of the solute. These refraction index detection instruments permit thereby the monitoring of solute concentration, an important determination for many forms of liquid chromatography. Another area of application of refractive index determination relates to measurement of sugar content of various fluids. Instruments make these measurement based on a determination of the difference of left and right refractive indices of the solution whose sugar content is to be determined. For example, the Swedish company Optilab manufactures such a unit under the Tecator brand name. This technique is described in detail in the U.S. Pat. No. 4,229,105 by Silverbage.

A variety of other techniques for measuring refractive index differences have been developed over the years. Some significant prior art includes the following:

U.S. Pat. No. 4,660,974 by Machler et al. describes the determination of the spectral characteristics of the refractive index of a fluid using white light illumination and examination of the resulting interfering component beams of light. The patent also contains numerous references to other types of interferometric methods.

U.S. Pat. No. 4,569,590 by Karny et al. describes a method of creating a reference Moire pattern with respect to a cell containing a reference fluid. Upon changing the fluid, the pattern changes with said changes being used to determine the refractive index of the changed fluid.

The U.S. Pat. No. 3,619,068 by Broerman describes a refractometer of particular importance for the field of liquid chromatography. It is comprised of two intersecting channels one of which carries the fluid whose refractive index is to be measured. The second channel intersects the first at an angle other than 90°. At the points of intersection the two sections of the second channel are sealed with polished transparent windows. One section contains a light source, the other a light detector. The light detector arm is filled with optical rods whose faces closest to the fluid are oriented so that the light transmitted through the fluid strikes the rods at approximately the critical angle of the fluid. As the refractive index of the fluid changes, the amount of light reaching the detector will change, permitting thereby the deduction of said fluid refractive index change.

BRIEF SUMMARY OF THE INVENTION

It is the major objective of my invention to monitor the refractive index of a fluid stationary within or flowing through a capillary surrounded by a transparent medium. This is accomplished by detecting the deviation of a fine beam of light after it has passed through the capillary, said displacement being due to the difference between the refractive index of the fluid and the transparent medium surrounding it. The transparent medium surrounding the capillary is of a refractive index higher than that of the fluid and the passage of the light beam is from the medium into the capillary at angle obtuse to the capillary axis and then exiting the capillary back into the medium. The deviation of the light beam from its straight line path is due to the differences of the corresponding refractive indices of the fluid and surrounding medium. The deviation will be greatest as the incident beam impinges on the capillary at an angle (measured with respect to the normal to the capillary axis) slightly less than the critical angle.

It is a further objective of my invention to provide a means for measuring the change of refractive index of a fluid at essentially the same physical position from which the fluid's light scattering properties are measured. This spatially coincident measurement is particularly important in the field of liquid chromatography, especially when applied to the technique of size exclusion or gel permeation chromatography.

Another objective of my invention is the deduction of the concentration of dissolved substances in the fluid, since a changing concentration of a dissolved solute will cause corresponding changes in the refractive index of the resulting solution. Such changes in concentration can be quantitated by converting said beam deviation into corresponding changes in concentration.

My invention will be particularly useful when applied to the light scattering cell of the above referenced U.S. Pat. No. 4,616,927 of which I am a co-inventor. Said patent describes an important type of light scattering cell permitting measurement of the light scattering properties of solutions with minimal interference from light scattered at the cell interfaces.

DETAILS OF THE INVENTION

Figure 1:
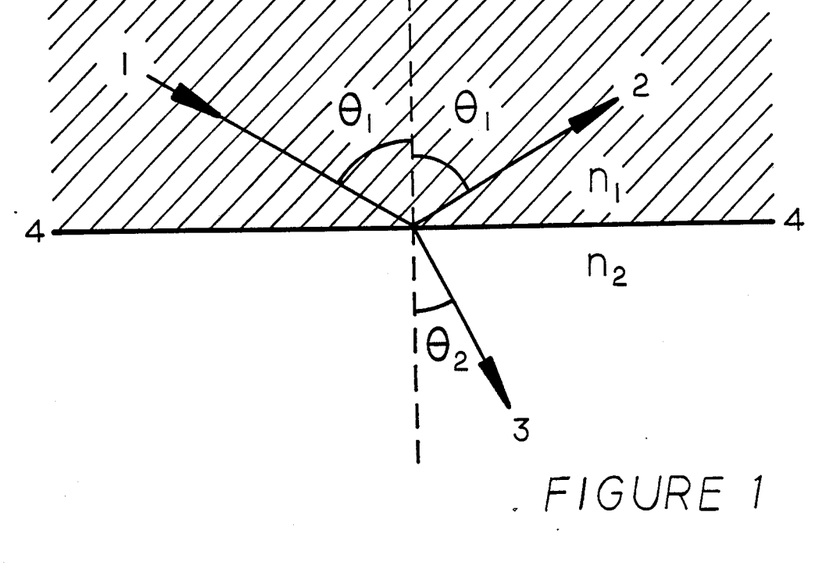
FIG. 1 illustrates Snell's Law for the refraction and reflection of a ray of light.

FIG. 1 presents a diagram of the refraction and reflection of a light ray 1 in a transparent medium of refractive index $n_1$, striking the plane interface 4 - 4 at an angle $\theta_1$, and entering a medium of refractive index $n_2$ The ray 2 is reflected at an angle $\theta_1$ and the ray 3 is refracted into medium 2 at an angle $\theta_1$. The relationship between the angles $\theta_1$ and $\theta_2$ is given by Snell's Law $$n_1 \sin \theta_1 = n_2 \sin \theta_2. \tag{1}$$

Snell's Law was derived by Huygens in the 17th Century from his wave description of light and more rigorously may be derived from Maxwell's equations directly. The resultant equations of refraction and reflection between media for which the refractive indices may be complex are often referred to as the Fresnel equations. FIG. 1 has been drawn for the case where $n_2 > n_1$. Consider for that case, the situation where the ray 1 just grazes the plane interface, i.e.

$$\theta_1 = \pi/2. \tag{2}$$

Equation (1) may be rewritten, therefore, as $$\eta_2 = \theta_c = \sin^{-1}(n_1/n_2). \tag{3}$$

Equation (3) so-written defines the critical angle $\theta_c$ so-named because reversing the ray direction from 3 defines an angle of incidence at the plane 4-4 from medium $n_2$ which represents the limiting angle in that medium. Any ray incident to the interface 4-4 from medium $n_2$ at an angle greater than $\theta_c$ will be perfectly reflected and no energy will be refracted into medium $n_1$. At the critical angle, a surface wave is said to be launched between the media and that surface wave is exponentially attenuated in the medium $n_1$. These surface or evanescent waves have been shown to have most interesting properties and are of importance for a number of devices and inventions in common use. A textbook by N. J. Harrick on "Internal Reflection Spectroscopy" or his article in volume 17 of Applied Spectroscopy (1987) should be consulted for some further explanations and interesting applications.

Figure 2:
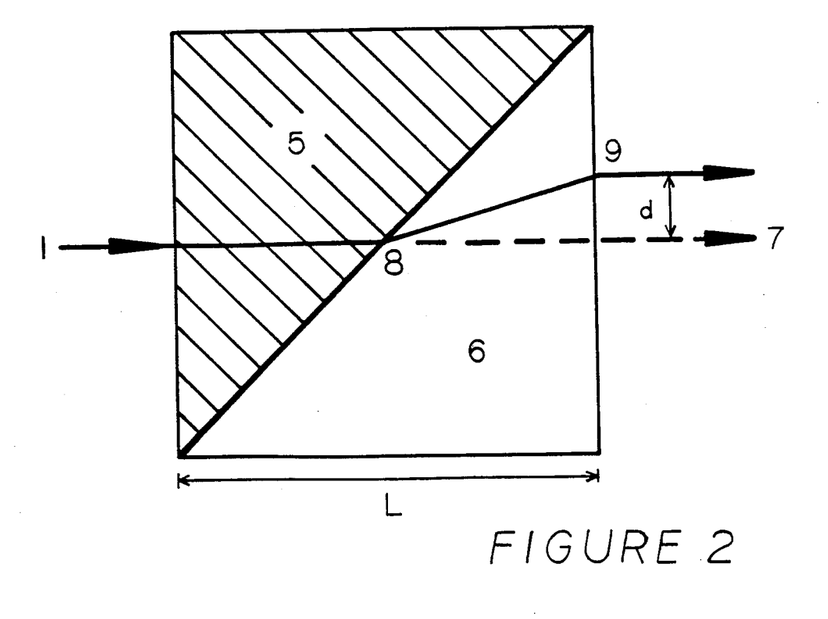
FIG. 2 shows the structure of a standard split prism cell used to measure the refractive index difference of two fluids.

FIG. 2 shows the structure of a conventional split prism device used to measure the difference of the refractive indices of two liquids contained, respectively, in triangular shaped regions 5 and 6. For small refractive index differences between the liquids, it may be shown that $$d = L(n_1 - n_2)/(2n_1) \tag{4}$$

where L is the width of the square structure. Note that the change in the displacement d is directly proportional to the difference of the refractive indices of the solutions.

Figure 3:
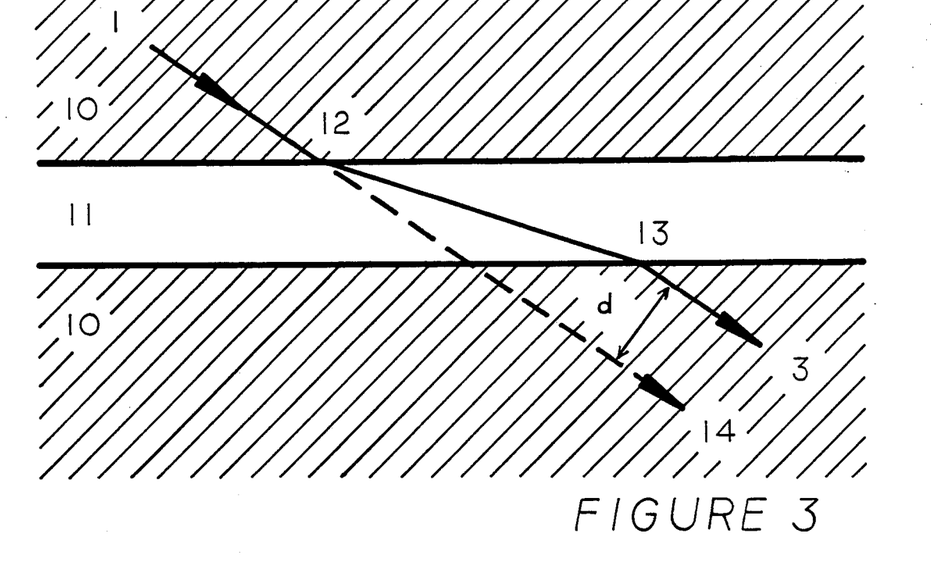
FIG. 3 shows the refractions of a ray traversing a liquid capillary within a transparent medium.

With these preliminaries, the details of my invention will be clearly understood by those skilled in the art. FIG. 3 presents the refraction of a ray of light passing through a liquid containing capillary. The ray 1 begins in transparent medium 10, strikes a capillary 11 at the point 12, is refracted by the difference of refractive indices between the medium 10 and liquid 11, strikes the opposite side of the capillary, and is refracted again as the ray 3 emerges at 13 into the medium 10 once again. The path of the indeviated ray 14 is indicated by the dotted line. The deviation, d, of the refracted beam with respect to the undeviated beam is also shown. For this figure, the geometry corresponds to all rays and the capillary lying in the same plane. If the refractive index of 11 were the same as that of the surrounding transparent medium 10, the beam 3 would be undeviated and superimposed on 14.

Let us now examine further the case where the liquid is of a refractive index less than the surrounding medium. For ease of discussion, we shall consider the transparent medium to be glass and the liquid to be a transparent fluid such as water or toluene or tetrahydrofuran or other so-called mobile phases used in forms of liquid chromatography. Alternatively these liquids are more commonly called solvents. This glass/mobile phase dichotomy is intended for illustrative purposes only. There are many other transparent solids and liquids by which means this invention is equally operative. For the discussion and explanation that follows we shall assume $$n_g > n_s, \quad (5)$$

where $n_g$ is the glass refractive index and $n_s$ is the refractive index of the solvent. The direction of the displacement d of FIG. 3 is characteristic of the relation of Eq.(5). As the refractive index of the liquid (solvent) increases because of the increased concentration of dissolved substances (solutes), the displacement of the refracted ray 3 will decrease and the refracted ray will approach co-linearity with the undeviated ray. Since characteristically the capillary will be of finite length, it is important to select the incident angle so that the ray displacement is not so great as to remove the ray completely, or so that it strikes ends of the capillary or the supporting structure. For example, if the angle of incidence from the glass was the critical angle per Eq. (3), then there would be no capillary traversing ray whatsoever.

Figure 4:
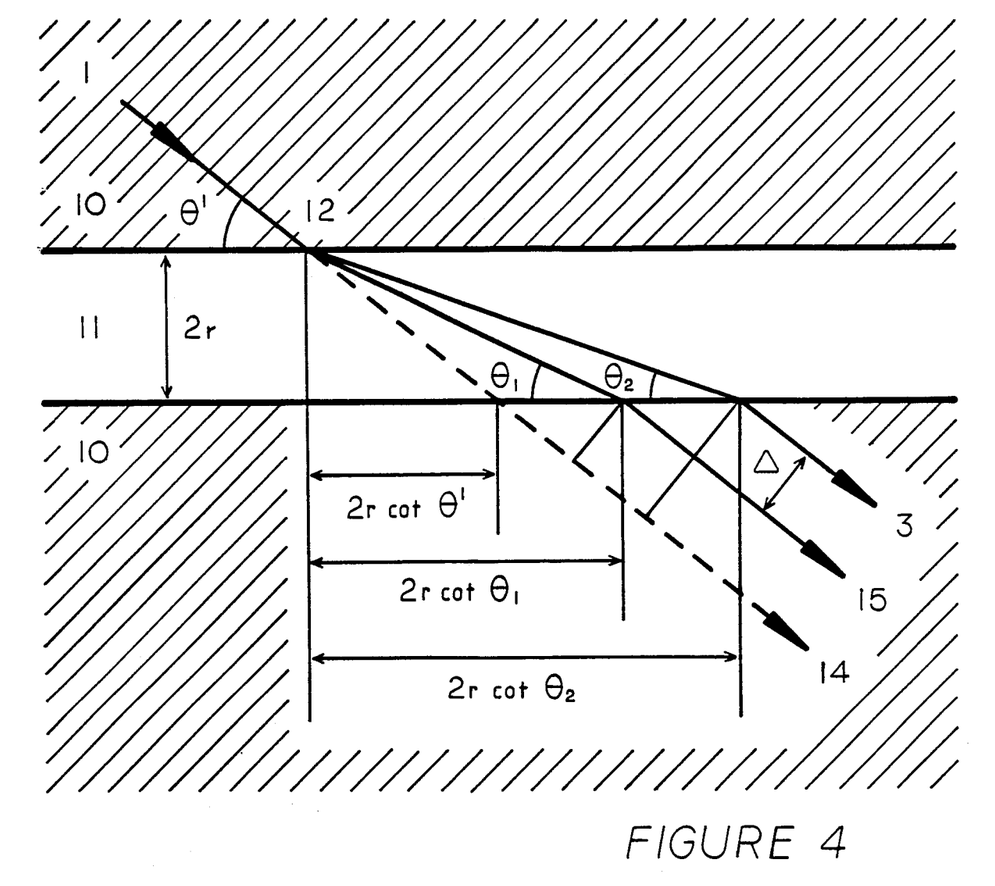
FIG. 4 shows a detail of the refractions responsible for the beam deviations arising from positive and negative refractive index increments of the fluid within a capillary.

Referring now to FIG. 4, we see the refractions and displacement of the ray 1 as it passes through the capillary 11, beginning and ending in the glass 10. The capillary is shown of diameter 2r. The incident ray 1 makes an angle $\theta'$ to the capillary axis. For this geometry, the conventional angle of incidence is $\pi/2 - \theta'$. The undeviated ray would appear as ray 14, ray 3 corresponds to the ray displaced by the pure solvent, and ray 15 displaced a distance $\Delta$ from ray 3 toward 14 is the ray corresponding to changes occurring due to a dissolved solute in the solvent causing a refractive index change $\Delta n$.

The various distances to the right of the perpendicular through the point of incidence 12 are labeled in the figure. Combining these results, the displacement $\Delta$ transverse to the ray 3 may be expressed simply in the form $$\Delta = 2r (\cot \theta_2 - \cot \theta_1) \sin \theta'. \quad (6)$$

The angles $\theta'$, and $\theta_1$ are related by Snell's Law $$n_g \sin (\pi/2 - \theta') = n_s \sin (\pi/2 - \theta_2) \quad (7)$$

or $$n_g \cos \theta' 32 n_s \cos \theta_2. \quad (8)$$

Further $$\cot \theta_2 = \frac{\cos \theta_2}{\sqrt{1 - \cos^2 \theta_2}} \quad (9)$$

$$= \frac{(n_g/n_s) \cos \theta'}{\sqrt{1 - (n_g/n_s)^2 \cos^2 \theta'}}$$

and similarly, $$\cot \theta_1 = [n_g/(n_s + \Delta n)] \cos \theta' / \sqrt{1 - (n_g/(n_s + \Delta n))^2 \cos^2 \theta'}. \quad (10)$$

Equation (6) may be readily evaluated given $\theta', n_g, \Delta n$ and $n_s$. Note furthermore that $$\theta' > \cos^{-1}(n_s/n_g), \quad (11)$$

since the right hand side of Eq. (11) corresponds to $\pi/2 - \theta_c$, where $\theta_c$ is the critical angle of Eq.(3). If $\theta'$ is less than or equal to $\cos^{-1}(n_s/n_g)$, then no ray enters the capillary 11.

In the limit $$(\Delta n/n_s)/(1 - \rho^2 \cos^2 \theta') >> 1, \quad (12)$$

Eq. (6) may be written in the approximate form $$\Delta \sim \frac{r\rho \sin 2\theta}{n_s \sqrt{1 - \rho^2 \cos^2 \theta'}} \left[ 1 + \frac{\rho^2 \cos^2 \theta'}{1 - \rho^2 \cos^2 \theta'} \right] \Delta n, \quad (13)$$

where $$\rho = n_g/n_s \quad (14)$$

Note that Eq. (13) confirms a linear displacement change, $\Delta$, with a linear refractive index change $\Delta n$, since $\theta', r, \rho$, and $n_s$ are fixed quantities. For $\Delta n$ much above $10^{-4}$ and $\theta'$ within 1° of the critical angle, this linear variation requires correction to second order.

Figure 5:
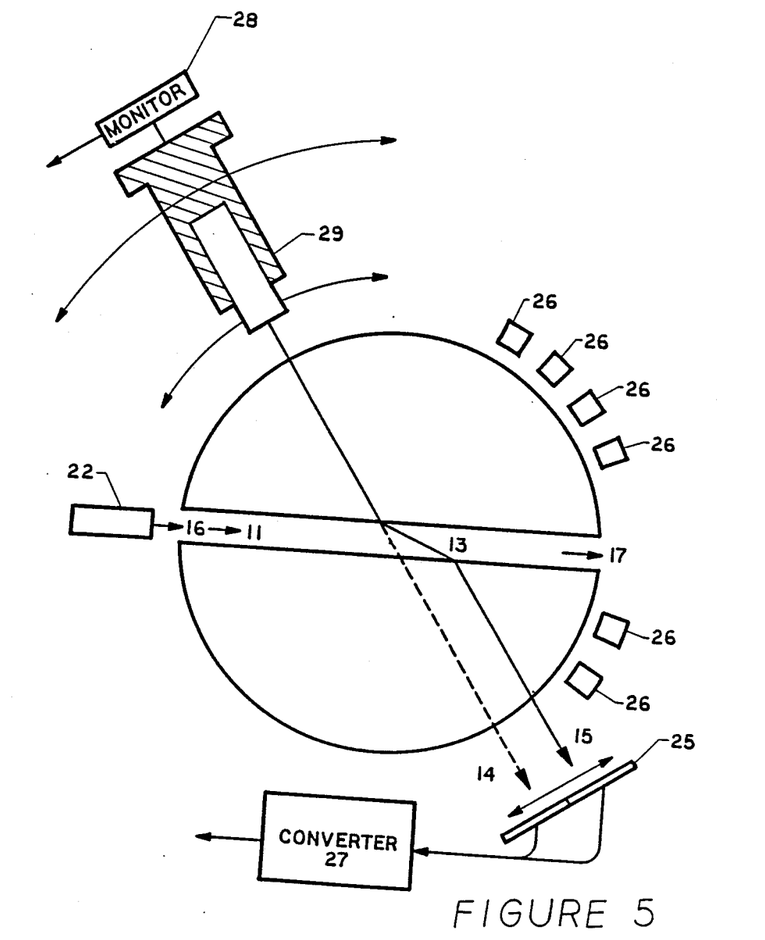
FIG. 5 shows a top view of the capillary-refracted rays' passage through the curved surface of the refraction cell of U.S. Pat. No. 4,616,927.

FIG. 5 shows a top view of the cylinder cell 10 of U.S. Pat. No. 4,616,927. The capillary 11 is bored along a cylinder diameter and polished. In its conventional configuration a light source 22 produces a beam incident through the capillary fluid from 16, exiting at 17. Scattered light detectors 26 are placed circumfrentially about the cylinder and lie in the plane of the capillary. These detectors are aimed toward the center of the capillary, and placed with faces parallel to the cylinder curved surface closest to them. Details are presented in the above referenced U.S. Patent. For purposes of the present refractometer invention, a secondary source of light 29 lying in the plane of the detectors, or otherwise above or below such plane, is directed toward the center of the capillary through which it would pass were it not for the refractions of the liquid within the capillary 11. The path of an undeviated ray is shown at 14, while the fluid has created the ray displaced therefrom by the liquid at 13. As the refractive index of the fluid within the glass capillary increases, the refracted ray will emerge at 15 where it is detected by an adjustable position sensitive detector 25 and converted into a numerical or analog representation at 27. A light source intensity monitor is shown at 28.

We will now examine Eqs. (6) and (10) for angles satisfying Eq. (11). As an example, let us take $n_g = 1.61655$ and $n_s = 1.3333$. Here $n_g$ is the refractive index of F2 glass at a wavelength of 632.8 nm. Such glass is of frequent use in optical fibers as well as the refraction cell of my coinvention U.S. Pat. No. 4,616,927, referred to at the beginning of this specification. F2 glass is commonly manufactured by Schott and Hoya Glass companies, among others. Let the solvent refractive index, $n_s$, correspond to water, a common solvent/mobile phase in liquid chromatography and let the incident wavelength be 632.8 nm. This is the wavelength of the most common He-Ne laser. For the stated glass and liquid, the incident ray must strike the capillary at an angle $\theta'$ greater than $$\cos^{-1}(1.333/1.61655) = 34.4°. \quad (15)$$

For purposes of subsequent calculation, we shall take the diameter of the capillary, $2d$, to be 1.5 mm, a commonly found dimension of the refraction cell above referenced.

Table 1 presents the displacement in mm of the refracted ray 3 of FIG. 4 from the undeviated ray 14 for the aforementioned values of $n_g$ and $n_s$. Also listed are the calculated transmittances of the ray 3 for vertical and horizontal polarizations of the incident ray. Vertically polarized light corresponds to plane polarized light for which the electric field is polarized perpendicular to the plane of the figure. Horizontally polarized light corresponds to plane polarized light whose electric field lies in the plane of the figure. The light transmitted through the capillary into the glass along ray 3 has a transmittance T that may be derived from the Fresnel relations presented, for example, by C. W. Ditchburn in his book "Light." At each glass/liquid interface, there is a reflected fraction R of the incident power. Thus, the light transmitted through the capillary is $$T = (1-R)^2. \quad (16)$$

The reflectance R for the case of horizontally polarized light (electric field lies in the plane of the capillary axis) is $$R_H = \tan^2(\theta' - \theta_1)/\tan^2(\theta' + \theta_1). \quad (17)$$

For vertically polarized incident light (electric field polarized perpendicular to the capillary axis), $$R_v = \sin^2(\theta' - \theta_1)/\sin^2(\theta' + \theta_1). \quad (18)$$

TABLE 1

| Ray displacement in mm for water filled capillary in F2 glass. | | | |
|---|---|---|---|
| $\theta'$ (degrees) | Displacement | $T_V$(%) | $T_H$(%) |
| 35 | 6.10 | 24 | 40 |
| 36 | 3.23 | 45 | 67 |
| 37 | 2.30 | 58 | 79 |
| 38 | 1.81 | 66 | 86 |
| 39 | 1.49 | 72 | 91 |
| 40 | 1.27 | 76 | 94 |
| 45 | 0.71 | 88 | 99 |

Note that the closer the incident ray 1 lies to the critical angle of 34.4°, the greater is the displacement and the smaller is the transmitted fraction for either polarization.

Next, consider the effect of a refractive index change in the capillary fluid of 0.0005, i.e. let the liquid refractive index increase to 1.3338. This is a change that might be encountered for a peak concentration of 5 mg/ml in a size exclusion chromatography experiment. The utility of a differential refractometer is directly related to its ability to monitor such changes in refractive index. The calculations of Table 2, which follow, include another column, viz. the displacement change with respect to the position of the pure water displacement.

TABLE 2

| Ray displacement and changes, $\Delta$, caused by a capillary solvent (water) refractive index increase of 0.0005 in F2 glass. | | | | |
|---|---|---|---|---|
| $\theta'$ (degrees) | Displacement | $\Delta$ | $T_V$(%) | $T_H$(%) |
| 35 | 5.90 | 0.194 | 25 | 42 |
| 36 | 3.19 | 0.043 | 46 | 67 |
| 37 | 2.28 | 0.021 | 58 | 80 |
| 38 | 1.79 | 0.013 | 66 | 87 |
| 39 | 1.48 | 0.009 | 72 | 91 |
| 40 | 1.26 | 0.007 | 76 | 94 |
| 45 | 0.70 | 0.002 | 88 | 99 |

Again we see that the most pronounced effects occur closest to the critical angle.

Consider now a second example where instead of F2 glass, we choose instead K5 glass whose refractive index at 632.8 nm is 1.52064. The critical angle (measured with respect to the capillary axis) is now 28.74° per Eq. (11).

TABLE 3

| Ray displacement in mm for water filled capillary in K5 glass. | | | |
|---|---|---|---|
| $\theta'$ (degrees) | Displacement | $T_V$(%) | $T_H$(%) |
| 29 | 8.98 | 16 | 24 |
| 30 | 3.44 | 46 | 60 |
| 31 | 2.30 | 60 | 75 |
| 32 | 1.75 | 69 | 84 |
| 33 | 1.42 | 76 | 89 |
| 35 | 1.03 | 83 | 94 |
| 40 | 0.58 | 92 | 99 |

Introducing a refractive index change of 0.0005 now yields the values shown in Table 4.

TABLE 4

| Ray displacement and change, $\Delta$, caused by a capillary solvent (water) refractive index increase of 0.0005 in K5 glass. | | | | |
|---|---|---|---|---|
| $\theta'$ (degrees) | Displacement | $\Delta$ | $T_V$(%) | $T_H$(%) |
| 29 | 8.28 | 0.698 | 18 | 26 |
| 30 | 3.37 | 0.071 | 46 | 61 |
| 31 | 2.27 | 0.030 | 61 | 76 |
| 32 | 1.74 | 0.017 | 70 | 84 |
| 33 | 1.41 | 0.012 | 76 | 89 |
| 35 | 1.02 | 0.007 | 84 | 94 |
| 40 | 0.58 | 0.003 | 92 | 99 |

As a final example, consider the solvent toluene whose refractive index is about 1.49, in F2 glass. The critical angle from Eq. (3) is now 22.82 degrees. Tables 5 and 6 present the corresponding data.

TABLE 5

| Ray displacement in mm for toluene filled capillary in F2 glass. | | | |
|---|---|---|---|
| $\theta'$ (degrees) | Displacement | $T_V$(%) | $T_H$(%) |
| 23 | 10.04 | 15 | 19 |
| 24 | 3.18 | 51 | 60 |
| 25 | 2.06 | 66 | 75 |
| 26 | 1.54 | 75 | 84 |
| 27 | 1.24 | 81 | 89 |
| 30 | 0.76 | 90 | 96 |
| 35 | 0.44 | 95 | 99 |

TABLE 6

| Ray displacement and change, $\Delta$, caused by a capillary solvent (toluene) refractive index increase of 0.0005 in F2 glass. | | | | |
|---|---|---|---|---|
| $\theta'$ (degrees) | Displacement | $\Delta$ | $T_V$(%) | $T_H$(%) |
| 23 | 8.81 | 1.228 | 18 | 22 |
| 24 | 3.10 | 0.084 | 52 | 61 |
| 25 | 2.03 | 0.034 | 67 | 76 |
| 26 | 1.53 | 0.020 | 76 | 84 |
| 27 | 1.22 | 0.013 | 81 | 89 |

TABLE 6-continued

Ray displacement and change, Δ, caused by a capillary solvent (toluene) refractive index increase of 0.0005 in F2 glass.

| θ' (degrees) | Displacement | Δ | $T_V$ (%) | $T_H$ (%) |
|---|---|---|---|---|
| 30 | 0.75 | 0.006 | 90 | 96 |
| 35 | 0.44 | 0.003 | 96 | 99 |

Measurement of the displacement change, Δ, may be achieved quite easily. Using a split photodiode, for example, of the type manufactured by United Detector Technology, changes less than 0.1 micrometer may be detected. Such a refractive change would correspond to a concentration change of the order of $10^{-4}$ ng/ml Referring to the examples presented, we note the following:

(1) The greatest displacement changes occur for incident light beam angles approaching the critical angle. The displacement change becomes smaller quite rapidly as the incident beam moves away from this critical angle.

(2) The displacement change increases with increasing glass/liquid refractive index difference.

(3) The transmission change, for both V and H incident polarizations, $dT/d\theta'$, decreases as the liquid refractive index increases.

Figure 6:
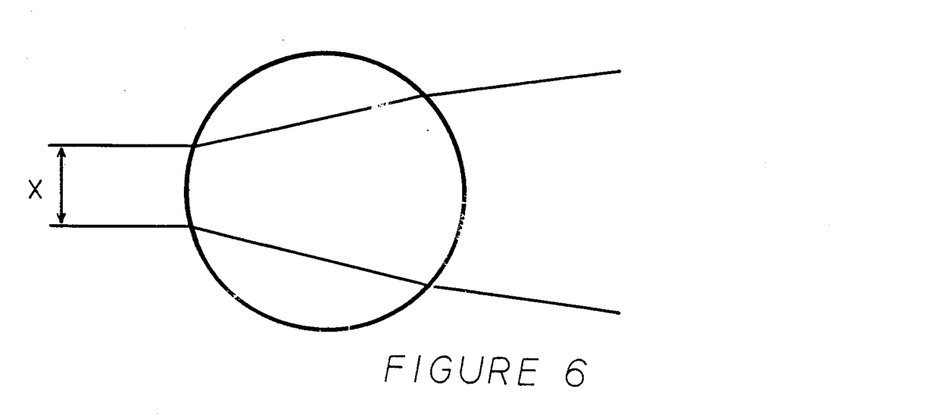
FIG. 6 shows the liquid capillary acting as a diverging cylindrical cell with respect to the incident light beam of finite cross section.

Note that a narrow beam of light of finite cross section X passing through the capillary will produce a flaired oblong refracted beam transverse to the refraction plane upon emerging from the capillary structure of FIG. 5. FIG. 6 presents a side view of a finite beam of diameter X passing through a capillary whose refractive index is less than that of the surrounding medium. Since the capillary refractive index is less than that of the glass, the capillary will act as a negative cylindrical lens. A split photodiode detector would be placed preferentially with its face nearly perpendicular to the emerging beam and its division axis along the flair direction.

Figure 7:
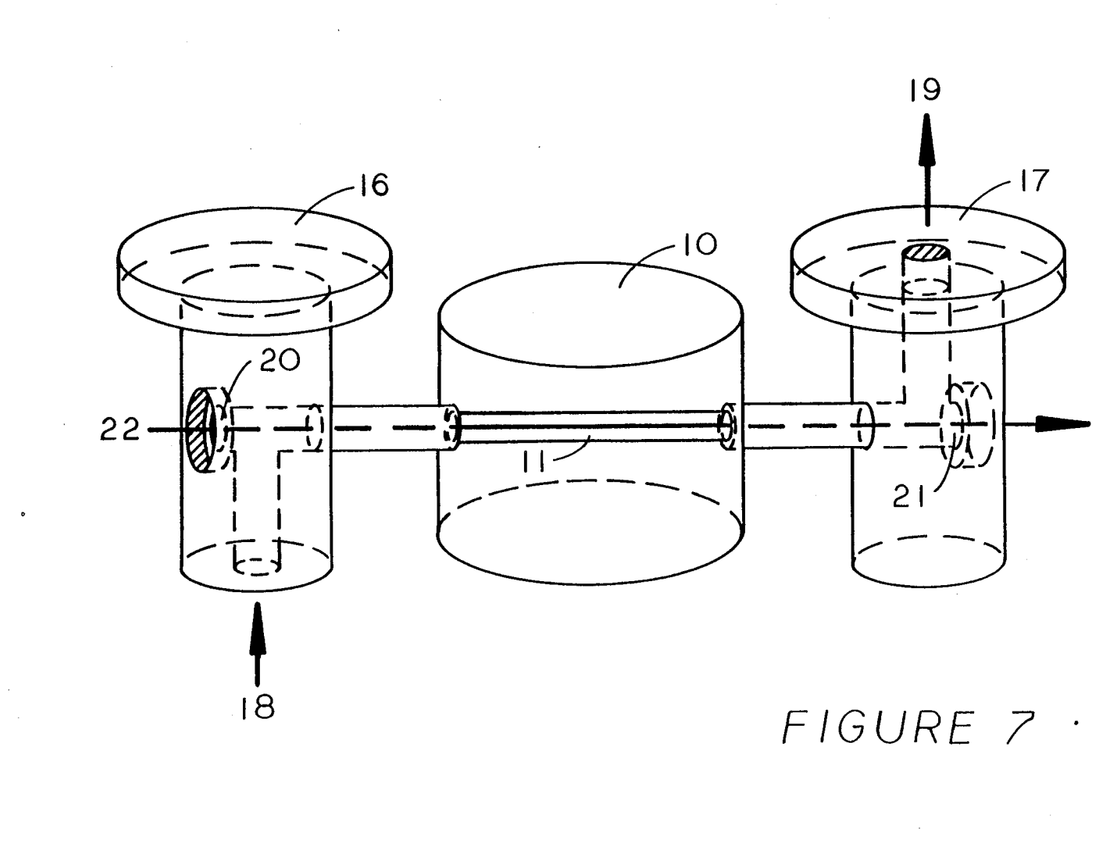
FIG. 7 shows the refraction cell of U.S. Pat. No. 4,616,927.

FIG. 7 is a drawing of the cylinder refraction cell and manifold structure described in U.S. Pat. No. 4,616,927. The cylindrical cell 10 is shown with the fine capillary 11 attached at either end by inlet and outlet manifold 16 and 17, respectively. The fluid sample is introduced at 18, pumped into the cell, and sent to waste at 19. Each manifold is fitted with a laser beam entrance or exit window, 20 or 21, respectively. The laser source used for scattering experiments produces a beam entering at 20, passing along the capillary 11 axis, and exiting through window 21. An array of detectors, not shown, lie circumfrentially about the cylinder cell in a plane parallel to the cylinder ends and coplanar with the capillary 11.

Figure 8:
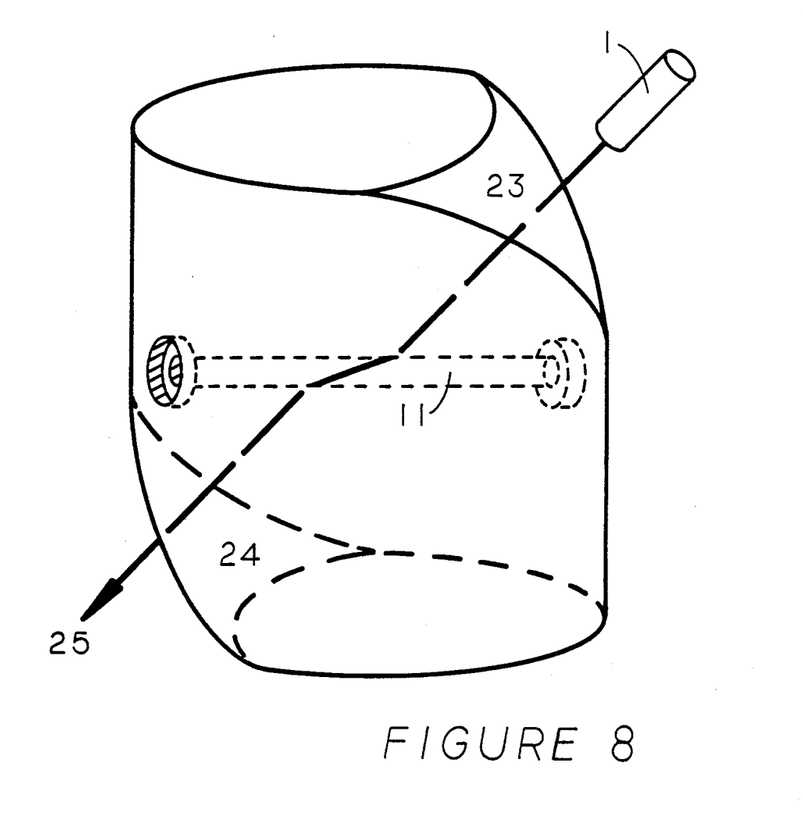
FIG. 8 shows a modified refraction cell permitting light beam incidence and emergence through curved surfaces outside of the standard detector plane.

The actual shape of the transparent region through which the capillary passes may be of many different forms, each form selected on the basis of the geometry and function of the region into which the differential refractometer is to be located. For example, for one preferred embodiment of the invention, the glass region would be in the form of the refraction cell disclosed in the previously referenced U.S. Pat. No. 4,616,927 by Phillips et al. and shown in FIG. 5. However, such an orientation of the incident light beam to the capillary axis could be effected equally well by positioning the source below the detection plane by means modifying the glass cell in the manner indicated in FIG. 8. Here the light beam 1 is incident on a circular face or other suitable shaped surface 23, passes through the capillary 11, is refracted thereby as has been discussed earlier, and then emerges through the similar and opposite surface 24 to be detected at 25. Note that the position sensing detector 25 and the incident light source 1 lie out of the conventional detection plane of the aforereferenced Phillips et al. patent. The capillary could be illuminated also from above, through the flat top of the cylinder, with detection below the cylinder base. In addition, the cylinder top and bottom surfaces may be modified to incorporate convex structures permitting normal incidence thereon of the rays required to intersect the capillary at angles near the glass/solvent critical angle.

Although the preferred and most common configuration of the capillary will be of cylindrical cross section, other forms may be used to equal advantage. For example, the cross section could be rectangular, being formed by combining planar polished transparent elements to yield a capillary void through which the fluid may flow, or in which it may be placed, of rectangular cross section. In addition, the capillary need not be straight since a slightly curving capillary, whose radius of curvature is large compared to the transverse dimensions of the capillary, may be useful for certain types of geometries.

Having described the elements of my invention together with some examples of glass-capillary structures that might be employed therein, I now present some preferred embodiments of the invention.

The ability to determine the refractive index change of a fluid in which a solute has been dissolved requires the following elements'

(A) A collimated light beam oriented with respect to the fluid bearing capillary at an angle somewhat less than the critical angle defined by the refractive indices of the entraining transparent medium (higher refractive index) and the solute-absent fluid (lower refractive index) given by Eq.(11). Preferentially, the illuminating light source 29 will be a laser unpolarized or polarized. Incident polarization can be plane or circular or combination thereof;

(B) Attachment means whereby the light beam of A may be positioned with respect to and rigidly attached to (C) A transparent refraction cell containing a finely polished capillary carrying said fluid therethrough; and (D) Position sensing means whereby the displacement of the refracted transmitted beam caused by a fluid refractive index change may be detected and quantified.

It is important to note that if the solute has a negative refractive index increment (dn/dc) with concentration, the angle of the incident beam preferentially would be oriented at a smaller angle than if dn/dc is positive. This will prevent the refracted beam from approaching the critical angles too closely thereby preventing any light from being refracted. For the Broerman device, described earlier, this type of an adjustment could not be effected. In addition, the Broerman device is directed to detecting intensity differences whereas the present device detects both displacement and intensity variations with most emphasis on the former.

In a preferred embodiment of the invention, the refraction cell would be of the cylindrical shape and form described in the Phillips, et al. patent. The light source would be a fine laser beam lying in the detector plane, oriented normal to the cylinder face, and entering the fluid bearing capillary at an angle (measured with respect to the normal to the capillary axis) slightly less than the critical angle defined by Eq.(3). After refraction through the capillary in the manner shown in FIG. 4 and emerging through the opposite face of the cylinder as detailed in FIG. 5, the beam is centered upon a position sensing element. The reference position of the beam with respect to said sensing element preferentially corresponds to the refracted position 3 caused by the pure solvent alone. Any change in refractive index of the solvent would cause a shift of the beam 15 from said reference position 3 which in turn would cause a change in the output signal of the position sensing device, such as shown at 25 in FIG. 8.

The output signal could be generated in different manners. For example, with a split photodiode of the type described previously, each half of the photodiode would be subjected to different levels of incident light flux caused by changes in the centering of the beam as well as intensity variations transverse to the beam due to different transmissivities of the refracted elements of the beam arising from its finite cross section and the corresponding slight differences of incident angles. A typical output would be generated by the difference of the two corresponding output currents or voltages. Since light sources of considerable short term stability are required for increased precision, the difference signal could be referenced to the light power incident on the structure. Said incident light power may be obtained from a reference beam incident on a different photodiode. For example, many lasers have a small amount of light energy leaking out through their rear laser mirror, said light being easily detected by a the simple of photodetector monitor fastened to the rear of the laser as indicated schematically by element 28 in FIG. 5. As the laser output varies, so too would the rear beam power. Alternatively incident reference power could be monitored with respect to a beam splitter at the emitting forward end of the laser. Such monitoring systems have been described in considerable detail in the copending application earlier referenced in this specification.

Note that the differential response of the position sensor as well as the light beam monitor should be converted to a numerical or analog representation for practical use. Thus a preferred output of the instrument would be a numerical representation of the change of refractive index of the solution relative to a previously measured or stored reference value. The most accurate values so-displayed would be generated internally or by external computer means to yield a value dn proportional to the ratio of the differential detector output divided by the incident light beam intensity. Since Eq. (6) suggest a proportionality which generally may not be quite linear as shown in Eq. (13), the proportionality factor as a function of $\Delta$ may be stored in computer means connected to the instrument for subsequent reference, may be generated and stored by means of a calibration procedure, and/or may be generated by external computer means If the unit is to be used on line, for example with a simultaneous light scattering measurement, then the analog signals generated by the instrument would be transmitted directly into an analog to digital multiplexing converter 27 for on-line use in another preferred embodiment of the invention.

Since the displacement, $\Delta$, is a monotonic function of the refractive index change, $\Delta n$, and said refractive index change will be directly proportional to the concentration change of the dissolved substance, the said displacement may be referred directly to the actual concentration of said dissolved substance. Thus referred to the displacement, d, of the pure liquid, the measured displacement which induces a monotonic response in a detecting position sensing means may be used to generate a solute concentration value, c. Each displacement will correspond, therefore, to a specific concentration from the relation $$n = n_0 + (dn/dc) c, \quad (19)$$

or $$n - n_0 = \Delta n = (dn/dc) c \quad (20)$$

and $$c = \Delta n/(dn/dc), \quad (21)$$

where $n_0$ is the refractive index of the pure fluid absent dissolved substance and n is the refractive index of the fluid plus solute. dn/dc is easily measured by making a measurement of $\Delta n$ caused by a concentration change $\Delta c$, then extrapolating to the limiting value of $n/\Delta c$, i.e.

$$(dn/dc) = \lim (\Delta n/\Delta c). \ \Delta c \rightarrow 0 \quad (22)$$

Figure 9:
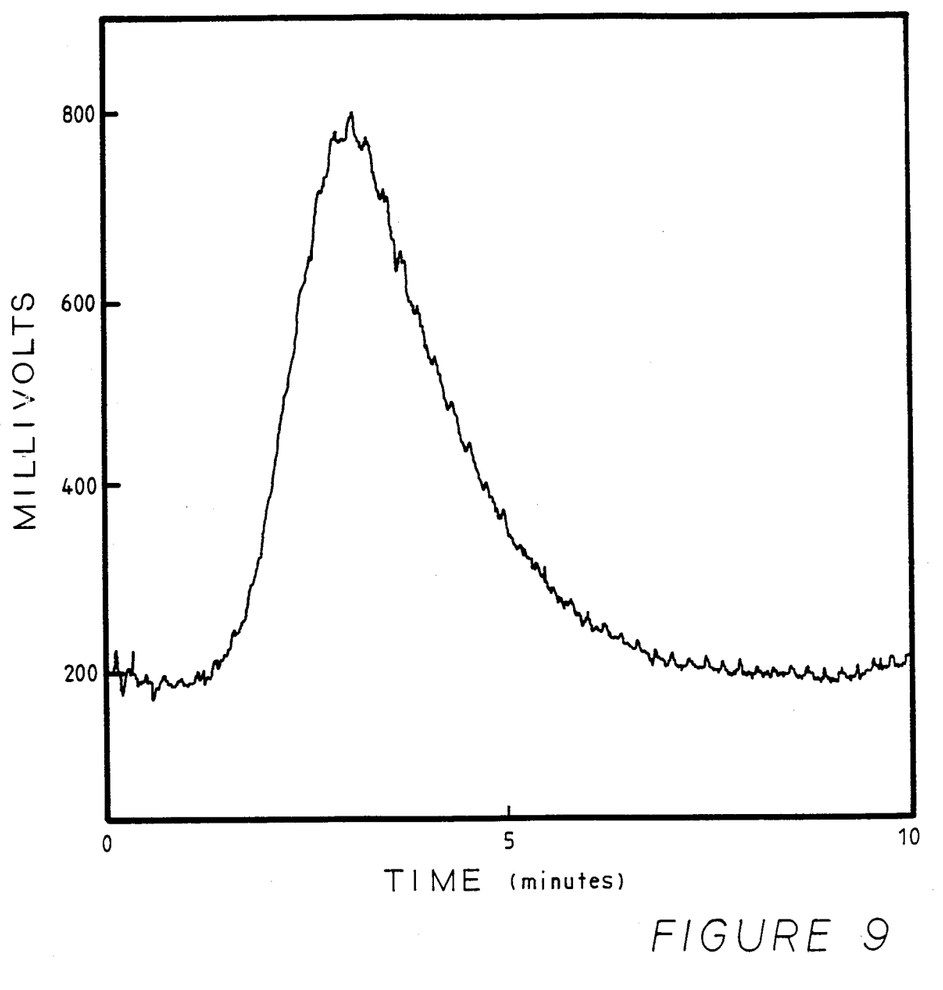
FIG. 9 shows the results of an early experimental measurement confirming the sensitivity of the present invention.

FIG. 9 shows the result of an early experimental confirmation of the invention. A 5 mW plane polarized laser beam was attached to a structure holding a refraction cell of the type described in the Phillips et al. patent. The wavelength of the laser was 632.8 nm, the cell refractive index was 1.61655, and the capillary was filled with water of refractive index 1.333. Injected into the capillary and pumped therethrough by means of a chromatography pump of the type manufactured by the Waters Company was a 20 microliter aliquot of a 0.1% dextran (in NaCl buffer) of approximate molecular weight 600,000. The change of refractive index with respect to concentration dn/dc was about 0.10. The difference of the two signals produced by the United Detector Technology split photodiode was amplified to produce the FIG. 9 plot of voltage versus time. Since the pump was operating at a speed of 0.5 ml/minute, the time scale also corresponds to the so-called retention volume obtained by multiplying time by the factor 0.5 ml/min. The small spikes superimposed on the curve arose from pump pulsations causing the structure to move slightly relative to the laser and detector source. These are easily removed by incorporating said refracted cell elements into a stationary structure. The breadboard configuration used to make these early measurements was assembled without particular attention to structural stability.

Although the impressive results of FIG. 9 were generated using a continuous wave laser, further signal enhancement would be achieved by modulating the laser beam by electrical or chopper means. At a frequency above the cutoff frequency of the standard multi-angle detectors of the Phillips et al. device, the modulated refractive index signal would not be detected by the multi-angle detectors. Thus, the multi-angle scattering as well as the refractive index changes could be monitored simultaneously even though both were performed at the same wavelength using different laser sources. Alternatively, both sets of measurements could be interspersed, turning one laser off while the other was on. A further variation of the dual measurement could be performed using light sources of different wavelengths in combination with filters covering the multiangle scattering detectors and permitting thereby the selective detection of the appropriate signals with a narrow band pass filter covering the position sensitive detector corresponding to the wavelength of the refractometer light source and covering the multi-angle scattered light detectors with narrow band pass filters at the wavelength of the scattering light source. Many variations of these detection strategies will be clearly evident to those skilled in the art of light detection from fixed sources.

For each type of fluid of different refractive index, there will be a unique optimal angle at which the incident light beam should be set. Thus, unless said fluid be always the same, means should be provided to adjust the angle of the incident beam with respect to the capillary. Optimally, this angle will lie close to the critical angle, perhaps one or two degrees therefrom. Alternatively, the light source may be fixed and the capillary containing refraction cell rotated so that the beam/capillary angle setting may be adjusted thereby. Means should also be provided, as required, to orient the position sensing element that monitors the position of the refracted beam. Once the light beam/capillary angle has been set for the solvent selected, the adjustment of the position sensing element is straightforward' with the capillary filled with the pure solvent, the position sensing element is set at a position that will yield a null electrical signal. Alternatively, it could be placed at a position yielding a small signal relative to those it would generate with increasing solute concentration. Depending upon the actual physical structure of the position sensing element, there could be many similar orientations thereof, as will be readily apparent to those skilled in the art.

In closing this discussion of my invention, some further features are disclosed. The light beam, which would be preferably a laser generated beam, should be of a cross section less than the cross section of the capillary since only those elements of the beam striking the capillary will be refracted and, in a preferred embodiment, all elements of the incident light beam should be affected by refraction in the capillary. Further, as has been alluded to earlier, the best orientation of the capillary and light beam should be such that their center lines intersect. Any other orientation would correspond to a partial grazing by the incident beam. The symmetric spatial intersection of the two axes will insure further the symmetrical refraction of the incident light beam by the capillary with respect to the plane defined by these two lines.

We note, furthermore, from Eq. (6) that the displacement of the refracted beam, $\Delta$, with respect to the incident beam, increases as the capillary diameter, $2r$, increases. The capillary itself, therefore, must be long enough to accomodate both the refracted beam as well as the internally reflected beam without said beams striking the capillary terminations or any other similar obstacles. Such obstacles would result in secondary reflections by said beams and these reflections are generally unwanted sources of stray light. Since the sensitivity of the refractometer increases as the diameter of the capillary, the optimal cell may be larger than the standard refraction cell, which is about 22 mm. However, from the chromatography point of view, a larger capillary volume will result in a greater band broadening of the solute contained therein. Thus a judicious tradeoff of design parameters must be made.

While there has hereinbefore been presented what is at present considered to be the preferred embodiments of the method and apparatus for measuring the refractive index changes within the fluid bearing capillary, it will be apparent to those of ordinary skill in the art that many modifications and variations may be made therefrom without departing from the true spirit and scope of the invention. All such variations and modifications, therefore, are considered to be a part of the invention.

What is claimed is:

1. A differential refractometer for measuring the refractive index change of a fluid, caused by a change in the concentration of a dissolved solute therein, comprised of
   A. a fluid bearing capillary within a transparent medium, said medium being of a refractive index greater than that of said capillary borne fluid;
   B. a light source producing a fine light beam coplanar with said capillary, said beam being directed to pass through said transparent medium and to intersect said fluid bearing capillary causing thereby said light beam to pass from said transparent medium after thereby having been twice refracted by said fluid bearing capillary;
   C. a refracted beam detector element receiving said twice refracted beam and which is responsive to the displacement of said twice refracted beam caused by refractive index change of said fluid due to said dissolved solute and producing a signal corresponding to said displacement;
   D. conversion means whereby said refracted beam displacement signal may be converted into a direct numerical or analog representation of $dn/dc$ where $dn$ is the refractive index change of said fluid caused by a concentration change $dc$ of said solute within said fluid.

2. The refractometer of claim 1 where said light beam is oriented with respect to said capillary at an angle slightly less than the critical angle $\theta_c$ where $$\theta_c = \sin^{-1}(n_s/n_g),$$

and $n_s$ is the refractive index of said capillary borne fluid and $n_g$ is the refractive index of said transparent medium.

3. The refractometer of claim 1 where said fine light beam is of a diameter less than the diameter of said capillary.

4. The refractometer of claim 1 where said fine light beam is generated by a laser.

5. The refractor of claim 1 where said fine light beam is adjustably fixed at different angles of incidence to said capillary.

6. The refractometer of claim 1 where said refracted beam detector element is a split two element photodiode.

7. The refractometer of claim 1 where said refracted beam detector element is adjustably fixed in position relative to said twice refracted beam so as to intercept suitably said twice refracted beam passing through said capillary.

8. The refractometer of claim 1 where said capillary is provided with liquid handling means permitting the injection of fluid therethrough.

9. The refractometer of claim 1 where said refractometer incorporates a second light source producing a second beam passing parallel to and through the capillary within the transparent medium and incorporates also a set of detectors coplanar with said capillary axis so that said refractometer serves also as a scattered light detector.

10. The refractometer of claim 1 where said transparent medium is in the shape of a right circular cylinder and said capillary passes through said cylinder along a diameter thereof.

11. The refractometer of claim 1 where said fine light beam source is provided with a means to monitor a value proportional to the intensity magnitude of said incident light beam and said displacement value is divided by said intensity magnitude value prior to conversion into said fluid refractive index change.

12. The refracted beam detector element of claim 7, where said fixed position of said element is adjusted such that the signal produced thereby is null when said fluid is absent said solute.

13. The refractometer of claim 1 where the angle of incidence of said fine light with respect to said fluid bearing capillary is adjustable.

14. The refractometer of claim 1 where said refracted beam detector element is responsive to the intensity of said twice refracted beam.

15. A method for measuring the refractive index change of a fluid caused by a change in the concentration of a dissolved solute therein, comprising the steps of
   A. providing a fluid bearing capillary within a transparent medium, said medium being of refractive index greater than that of said capillary borne fluid;
   B. illuminating said capillary by a coplanar fine light beam fixed and directed to pass through said transparent medium and intersect said capillary so that said light beam passes from said transparent medium into said capillary, through said capillary, and back out into said transparent medium after thereby having been twice refracted by said fluid bearing capillary;
   C. detecting the displacement of said twice refracted beam by position sensor means, where said displacement is caused by the refractive index change of said fluid due to said dissolved solute, and said detected displacement is converted into a value proportional to said displacement;
   D. converting said displacement value into a direct numerical or digital form representative of dn/dc where dn is the refractive index change of said fluid caused by a concentration change dc of said solute within said fluid.

16. The method of claim 15 where said light beam is oriented with respect to said capillary at an angle slightly less than the critical angle $\theta_c$ where $$\theta_c = \sin^{-1}(n_s/n_g),$$

and $n_s$ is the refractive index of said capillary borne fluid and $n_g$ is the refractive index of said transparent medium.

17. The method of claim 15 where said light beam is of a diameter less than the diameter of said capillary.

18. The method of claim 15 where said fine light beam is generated by a laser.

19. The method of claim 15 where said fine light beam is adjustably fixed at different angles of incidence of said capillary.

20. The method of claim 15 where said position sensor means is a split two element photodiode.

21. The method of claim 15 where said position sensor means is adjustably fixed so as to intercept said twice refracted light beam passing through said capillary.

22. The method of claim 15 where said capillary is provided with liquid handling means permitting the injection of fluid therethrough.

23. The method of claim 15 where said method incorporates a second light beam passing through and parallel to said capillary and said capillary is surrounded by a set of associated coplanar detectors positioned about said transparent medium so that light scattered in the plane of said coplanar detectors is detected thereby.

24. The method of claim 15 where said transparent medium is in the shape of a right circular cylinder and said capillary passes through said cylinder along a diameter thereof.

25. The method of claim 21 where said fixed position of said position sensor means is adjustably fixed such that the signal produced therefrom is null when said fluid is absent said solute.

26. The method of claim 15 where said fine light beam is monitored by a monitor means producing a monitor signal directly proportional to the intensity of said fine light beam before entering said capillary so that said displacement value is divided by said monitor signal before conversion into numerical or digital form representative of dn/dc.

27. A method for measuring the refractive index change of a fluid caused by a change in the concentration of a dissolved solute therein, comprising the steps of
   A. providing a fluid bearing capillary within a transparent medium, said medium being of refractive index greater than that of said capillary borne fluid;
   B. illuminating said capillary by a coplanar fine light beam fixed and directed to pass through said transparent medium and intersect said capillary so that said light beam passes from said transparent medium into said capillary, through said capillary, and back out into said transparent medium after thereby having been twice refracted by said fluid bearing capillary;
   C. detecting the intensity change of said twice refracted beam by detector means, where said intensity change is caused by the refractive index change of said fluid due to said dissolved solute, and said intensity change is converted into a value proportional to said refractive index change;
   D. converting said intensity change into a direct numerical form representative of dn/dc where dn is the refractive index change of said fluid caused by a concentration change dc of said solute within said fluid.

28. The method of claim 27 where said light beam is oriented with respect to said capillary at an angle slightly less than the critical angle $\theta_c$ where $$\theta_c = \sin^{-1}(n_s/n_g),$$

and $n_s$ is the refractive index of said capillary borne fluid and $n_g$ is the refractive index of said transparent medium.

29. The method of claim 27 where said light beam is of a diameter less than the diameter of said capillary.

30. The method of claim 27 where said fine light beam is generated by a laser.

31. The method of claim 27 where said fine light beam is adjustably fixed at different angles of incidence to said capillary.

32. The method of claim 27 where said intensity sensor is adjustably fixed so as to intercept said twice refracted light beam passing through said capillary.

33. The method of claim 27 where said method incorporates a second light beam passing through and parallel to said capillary and said capillary is surrounded by a set of associated coplanar detectors positioned about said transparent medium so that light scattered in the plane of said coplanar detectors is detected thereby.

34. The method of claim 27 where said transparent medium is in the shape of a right circular cylinder and said capillary passes through said cylinder along a diameter thereof.

35. The method of claim 27 where said fine light beam is monitored by a monitor means producing a monitor signal directly proportional to the intensity of said fine light beam before entering said capillary so that said intensity change value is divided by said monitor signal before conversion into numerical or digital form representative of dn/dc.

* * * * *